United States Patent [19]

Miwa et al.

[11] Patent Number: 4,769,499

[45] Date of Patent: Sep. 6, 1988

[54] PROCESS FOR SEPARATION OF SUBSTITUTED BENZENE ISOMERS

[75] Inventors: Kishio Miwa; Yukiko Nagaoka, both of Kamakura; Takehise Inoue, Tokyo, all of Japan

[73] Assignee: Toray Industries, Inc., Tokyo, Japan

[21] Appl. No.: 49,711

[22] Filed: May 12, 1987

Related U.S. Application Data

[62] Division of Ser. No. 785,488, Dec. 13, 1985, which is a division of Ser. No. 515,927, Jul. 20, 1983, Pat. No. 4,571,441.

[30] Foreign Application Priority Data

Dec. 28, 1982 [JP] Japan .................................. 57-231207

[51] Int. Cl.[4] ........................ C07C 37/68; C07C 37/82
[52] U.S. Cl. .................................. 568/758; 568/749; 568/750; 568/751

[58] Field of Search ................. 568/750, 749, 751, 758

[56] References Cited

U.S. PATENT DOCUMENTS

| | | | |
|---|---|---|---|
| 4,124,770 | 4/1978 | Miyake | 568/758 |
| 4,254,062 | 3/1981 | Wambach et al. | 570/211 |
| 4,356,311 | 10/1982 | Inoue et al. | 568/758 |
| 4,386,225 | 5/1983 | Neuzil | 568/758 |

Primary Examiner—Werren B. Lone
Attorney, Agent, or Firm—Austin R. Miller

[57] ABSTRACT

A substituted benzene isomer mixture containing a meta-substituted benzene or 1,3,5-substituted benzene is contacted with an adsorbent of a faujasite type zeolite containing a Ag cation and/or a Cu cation, whereby the meta-substituted benzene or 1,3,5-substituted benzene is separated and recovered as a raffinate component.

3 Claims, No Drawings

PROCESS FOR SEPARATION OF SUBSTITUTED BENZENE ISOMERS

This is a division of application Ser. No. 785,488, filed Dec. 13, 1985, which is a divisional of U.S. Ser. No. 515,927, filed July 20, 1983, now U.S. Pat. No. 4,571,441.

BACKGROUND OF THE INVENTION

1. Field of the Invention

This invention relates to a process for separating a meta-substituted benzene or 1,3,5-substituted benzene from a substituted benzene isomer mixture containing a meta-substituted benzene or 1,3,5-substituted benzene nuclearly substituted with a methyl, ethyl or hydroxyl group or a halogen atom.

2. Description of the Prior Art m-Chlorololuene among chlorotoluene (hereinafter referred to as "CT") isomers, m-dichlorotoluene among dichlorotoluene (hereinafter referred to as "DCB") isomers and 3,5-xylenol among xylenol (hereinafter referred to "XYOH") isomers are important as intermediate substances for agricultural chemicals and medicines, and m-diethylbenzene among diethylbenzene (hereinafter referred to as "DEB") isomers is valuable as a desorbent or an intermediate substances for a cross-linking agent. However, considerable difficulties are encountered in separation of these compounds by distillation because their boiling point are very close to those of their isomers.

If there is available an adsorbent capable of adsorbing a specific isomer selectively, separation of isomers will be accomplished at a high efficiency economically advantageously. An isomer capable of being strongly adsorbed in the adsorbent is selectively adsorbed in the adsorbent to be thereby separated as an extract component, and an isomer capable of being weakly adsorbed in the adsorbent is weakly adsorbed in the adsorbent to be thereby separated as a raffinate component. Thus, the isomer mixture is separated into the respective isomers.

U.S. Pat. No. 4,356,331 discloses a process in which a para-isomer is selectively adsorbed and separated from an alkyl phenol isomer mixture by using a zeolite of the Y type.

Furthermore, European Patent Application No. 81303609.2 discloses a process in which a para-isomer is selectively adsorbed and separated from a halogenated toluene isomer mixture by using a zeolite of the Y type.

However, these prior art references do not teach separation and recovery of meta-isomers.

U.S. Pat. No. 4,254,062 discloses separation of dichlorotoluene isomers by using a zeolite of the X or Y type, but separation of a 1,3,5-substituted isomer is not taught at all.

U.S. Pat. No. 4,124,770 discloses a process in which xylenol is separated from a mixture of xylenol and cresol by using a zeolite, but separation of a xylenol isomer mixture or cresol isomer mixture is not taught at all.

SUMMARY OF THE INVENTION

It is a primary object of the present invention to provide a process in which a meta-substituted benzene or 1,3,5-substituted benzene as described above is separated at a high purity from a starting mixture containing isomers thereof at a high efficiency by utilizing an adsorptive separation technique.

More specifically, in accordance with the present invention, there is provided a process for separating a meta-substituted benzene or 1,3,5-substituted benzene from a substituted benzene isomer mixture containing a meta-substituted benzene or 1,3,5-substituted benzene nuclearly substituted with a methyl, ethyl or hydroxyl group or a halogen atom, wherein the isomer mixture is contacted with a faujasite zeolite type adsorbent containing a Ag cation and/or a Cu cation whereby the meta-substituted benzene or 1,3,5-substituted benzene is separated and recovered as a raffinate component.

DETAILED DESCRIPTION OF THE INVENTION

Typical instances of the meta-substituted benzene to which the present invention is applied are m-CT, m-DCB and m-DEB, and typical instances of the 1,3,5-substituted benzene are 3,5-XYOH and 1,3,5-trimethylbenzene.

The faujasite type zeolite that is used in the present invention is a crystalline aluminosilicate represented by the following formula:

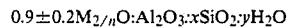

$$0.9 \pm 0.2 M_{2/n}O : Al_2O_3 : xSiO_2 : yH_2O$$

wherein M stands for a cation, and n indicates the valency of the cation M.

The faujasite type zeolite is classified into X and Y types. In the X type, x is a number of $2.5 \pm 0.5$, and in the Y type, x is a number of from 3 to 6. In the present invention, a zeolite of the Y type in which x, that is, the $SiO_2/Al_2O_3$ ratio, is in the range of from 3 to 6 is preferred. Zeolites of the Y type are described in detail in U.S. Pat. No. 3,130,007.

In the above formula, y differs according to the degree of hydration.

M is a cation. Ordinarily, a zeolite of the Y type in which M is sodium is available. In the present invention, silver and/or copper should be introduced as the cation into the adsorbent by the ion exchange. Any of known ion exchange processes can optionally be adopted. Ordinarily, the ion exchange is effected with an aqueous solution containing a nitrate of a required cation. Of course, an aqueous solution containing other water-soluble salt such as a chloride instead of the nitrate may be used.

When a faujasite type zeolite containing silver and/or copper as the cation is prepared, it is preferred that a sodium or potassium type faujasite be used as the starting material to be subjected to the ion exchange.

The faujasite type zeolite adsorbent may contain a cation other than silver and copper. For example, a metal of the group IA, IIA, IIIA or IVA or a proton may be contained. K and Na are especially preferred as the cation other than silver and copper.

The proportions of these cations differ according to the kind of the meta-substituted benzene or 1,3,5-substituted benzene to which the present invention is applied.

In case of m-CT, m-DCB or m-DEB, the Ag cation preferably occupies 5 to 90 mole% of all the cations and the K cation preferably occupies 10 to 95 mole% of all the cations. It is especially preferred that the proportion of the Ag cation be 10 to 50 mole% and the proportion of the K cation be 50 to 90 mole%. In case of 3,5-XYOH, the Ag and/or Cu cation preferably occupies 5 to 100 mole%, especially 15 to 100 mole%, of all the cations.

The adsorptive separation of a meta-substituted benzene or 1,3,5-substituted benzene by using the specified adsorbent according to the present invention may be accomplished by a chromatographic separation method or a continuous adsorptive separation method using a simulated moving bed.

According to the adsorptive separation method using a simulated moving bed, a plurality of absorbing chambers filled with an adsorbent are used and the following adsorption operation, concentration operation and desorption operation described below are continuously carried out in a cycle as the basic operations.

(1) Adsorption Operation

The starting mixture is contacted with the adsorbent whereby the component capable of being strongly adsorbed is selectively adsorbed. The remaining component capable of being weakly adsorbed is recovered as the raffinate component together with a desorbent described below.

(2) Concentration Operation

The adsorbent having absorbed therein the component capable of being strongly adsorbed is contacted with a part of an extract described below, whereby the component capable of being weakly adsorbed, which is left in the adsorbent, is expelled and the component capable of being strongly adsorbed is purified.

(3) Desorption Operation

The purified component capable of being strongly adsorbed is expelled from the adsorbent by the desorbent, and is recovered as the extract component together with the desorbent.

The intended meta-substituted benzene or 1,3,5-substituted benzene is separated and recovered as the raffinate component, that is, as the substance capable of being weakly adsorbed.

The desorbent used in the above-mentioned adsorptive separation method or the developer used in the chromatographic separation method is preferably a compound capable of being easily separated by distillation from the intended meta-substituted benzene 1,3,5-substituted benzene.

In the case where the intended substance is m-CT or m-DCB, an alkyl-substituted aromatic hydrocarbon or a chlorine-substituted aromatic hydrocarbon is preferred as the desorbent. Toluene, xylene, dichlorotoluene and chloroxylene are especially preferred.

In the case where the intended substance is m-DEB, toluene, xylene and trimethylbenzene are especially preferred as the desorbent.

In the case where the intended substance is 3,5-XYOH, oxygen-containing compounds, for example, alcohols having 3 to 6 carbon atoms such as n-propyl alcohol, n-butyl alcohol, isobutyl alcohol, sec-butyl, alcohol, amyl alcohol and hexanol, and ketones having 4 to 6 carbon atoms such as diethyl ketone, ethyl isopropyl ketone and diisopropyl ketone, are preferably used as the desorbent.

In the case where the intended substance is 1,3,5-trimethylbenzene, toluene, xylene and diethylbenzene are preferably used as the desorbent.

Furthermore, n-paraffin, isoparaffin, cycloparaffin or an aromatic hydrocarbon may be used as a diluent.

The adsorptive separation is carried out at a temperature of from room temperature to 350° C., preferably from 50° to 250° C., under a pressure of from atmospheric pressure to 50 Kg/cm²G, preferably from atmospheric pressure to 40 Kg/cm²G. In the present invention, the adsorptive separation may be carried out either in the vapor phase or in the liquid phase. However, in order to prevent occurrence of an undesirable side reaction in the starting mixture or desorbent, it is preferred that the operation be carried out at a low temperature in the liquid phase. If the starting mixture containing 3,5-XYOH is solid at the above-mentioned operation temperature, a hydrocarbon having a low solidification point may be used as a solvent.

The process of the present invention will now be described in detail with reference to the following examples.

In the examples, the adsorbing characteristic of the adsorbent is expressed by the following adsorptive selectively $\alpha$:

$$\alpha_{A/B} = \frac{[(\text{weight percent of component } A)/(\text{weight percent of component } B)]_S}{[(\text{weight percent of component } A)/(\text{weight percent of component } B)]_L}$$

In the above formula, S designates the adsorbed phase and L designates the liquid phase equilibrated with the absorbed phase.

If the value $\alpha$ is larger than unity, the component A is selectively adsorbed, and if the value $\alpha$ is smaller than unity, the component B is selectively adsorbed. If the value $\alpha$ is more larger than unity (or is smaller than unity and closer to zero) in the adsorbent, the adsorptive separation of the components A and B becomes easier.

EXAMPLE 1

Alumina sol was added as a binder to a powder of a zeolite of the Na-Y type ("SK-40" supplied by Union Carbide Corporation) in an amount of 10% by weight as Al₂O₃. A granulation product having a size of 24 to 32 mesh was obtained by extrusion molding from the mixture. The granulation product was dried at 100° C., calcined at 500° C. for 1 hour and then treated with an aqueous solution of potassium nitrate to replace more than 90% of the sodium ion with the potassium ion and thereby prepare an adsorbent of the K-Y type.

The zeolite of the K-Y type was treated at 60° C. with an aqueous solution of silver nitrate containing a silver ion in an amount corresponding to 10 to 60 mole% of the cation K in the zeolite of the K-Y type to prepare an adsorbent of the Ag-K-Y type.

In order to determine the selectivity of this adsorbent of the Ag-K-Y type for adsorption of chlotoluene isomers, about 2 g of the above adsorbent sintered at 500° C. for 1 hour and about 2.5 g of a liquid-phase mixture which comprises chlorotoluene isomers were charged in an autoclave having an inner capacity of 5 ml and heated at 110° C. for 1 hour while conducting stirring now and then.

A liquid-phase mixture charged comprised n-nonane, p-chlorotoluene, m-chlorotoluene and o-chlorotoluene at a weight ratio of 1:1:1:1.

n-Nonane was added as the internal standard substance for the gas-chromatographical analysis, and it was substantially inactive relatively to the adsorption under the experimental conditions. The composition of the liquid-phase mixture after the contact with the adsorbent was analyzed by the gas chromatography, and the adsorption selectivities for the chlorotoluene isomers were calculated according to the above-mentioned formula. The obtained results are shown in Table 1.

TABLE 1

| Run No. | Amount of Ag Ion in Treating Liquid [Ag/(K—Y) molar ratio] | $\alpha_{o/m}$ | $\alpha_{p/m}$ |
|---|---|---|---|
| 1 | 0.1 | 1.30 | 1.80 |
| 2 | 0.2 | 1.35 | 1.62 |
| 3 | 0.3 | 1.50 | 1.55 |
| 4 | 0.4 | 1.55 | 1.45 |
| 5 | 0.5 | 1.50 | 1.40 |
| 6 | 0.6 | 1.45 | 1.27 |

EXAMPLE 2

The adsorbent No. 4 shown in Table 1 of Example 1 was subjected to the ion exchange at a solid/liquid ratio of 5 by using an aqueous solution containing 7.8% by weight of potassium nitrate and an aqueous solution containing 0.6% by weight of ammonium sulfate.

The adsorptive selectivities of the resulting adsorbent for the chlorotoluene isomers were determined in the same manner as described in Example 1. It was found that $\alpha_{p/m}$ was 1.57 and $\alpha_{o/m}$ was 1.52.

COMPARATIVE EXAMPLE 1

Faujasite type zeolites in which the content of the single cation component was nearly 100% were tested in the same manner as described in Example 1, and the adsorptive selectivities for the chlorotoluene isomers were determined. The obtained results are shown in Table 2.

TABLE 2

| Adsorbent | $\alpha_{o/m}$ | $\alpha_{p/m}$ |
|---|---|---|
| Na—Y($SiO_2/Al_2O_3$ = 3.2) | 1.02 | 0.92 |
| K—Y($SiO_2/Al_2O_3$ = 3.2) | 1.10 | 0.85 |
| Na—Y($SiO_2/Al_2O_3$ = 4.8) | 0.91 | 0.68 |
| K—Y($SiO_2/Al_2O_3$ = 4.8) | 1.16 | 1.89 |
| Ca—Y($SiO_2/Al_2O_3$ = 4.8) | 1.05 | 1.16 |
| Na—X($SiO_2/Al_2O_3$ = 2.5) | 1.05 | 1.03 |
| K—X($SiO_2/Al_2O_3$ = 2.5) | 1.20 | 0.78 |
| Ca—X($SiO_2/Al_2O_3$ = 2.5) | 1.18 | 0.45 |
| Ba—X($SiO_2/Al_2O_3$ = 2.5) | 0.89 | 1.61 |
| Ag—Y($SiO_2/Al_2O_3$ = 4.8) | 1.38 | 0.99 |

COMPARATIVE EXAMPLE 2

The adsorbent of the K-Y type prepared in Example 1 was subjected to the ion exchange treatment with an aqueous solution containing an ion other than potassium in an amount corresponding to 10 mole% of the potassium cation in the adsorbent. The adsorptive selectivities of the resulting adsorbent for the chlorotoluene isomers were determined in the same manner as described in Example 1. The obtained results are shown in Table 3.

TABLE 3

| Adsorbent | $\alpha_{o/m}$ | $\alpha_{p/m}$ |
|---|---|---|
| Ba—K—Y | 1.18 | 2.15 |
| Mg—K—Y | 1.16 | 2.04 |
| Ca—K—Y | 1.22 | 1.61 |
| Sr—K—Y | 1.15 | 1.54 |
| Co—K—Y | 1.11 | 1.79 |

EXAMPLE 3

Alumina sol was added as a binder to a powder of a zeolite of the Na-Y type ("SK-40" supplied by Union Carbide Corporation) in an amount of 10% by weight as $Al_2O_3$, a granulation product having a size of 24 to 32 mesh was prepared by extrusion molding from the mixture. The granulation product was dried at 100° C. and calcined at 500° C. for 1 hour to prepare an adsorbent of the Na-Y type. Then, the adsorbent was treated with an aqueous solution of potassium nitrate to replace at least 90% of the sodium ion with potassium and thereby prepare an adsorbent of the K-Y type.

Then, the zeolite of the K-Y type was treated at 60° C. with an aqueous solution of silver nitrate containing a silver ion in an amount corresponding to 30 mole% of the K cation, whereby adsorbent of the 30% Ag-K-Y type was prepared.

In order to determine the adsorptive selectivities of the above-mentioned 3 kinds of the adsorbents for DCB isomers, about 2 g of the adsorbent calcined at 500° C. for 1 hour and about 2.5 g of a liquid-phase mixture which comprises DCB isomers were charged in an autoclave having an inner capacity of 5 ml, and was then heated at 110° C. for 1 hour while conducting stirring now and then. A liquid phase mixture charged to the autoclave comprised n-nonane, p-DCB, m-DCB and o-DCB at a weight ratio of 1:1:3:3, respectively. n-Nonane was added as the internal standard substance for the gas-chromatographical analysis, and n-nonane was substantially inactive relatively to the adsorption. The composition of the liquid phase mixture after the contact with the adsorbent was analyzed by the gas chromatography and the adsorptive selectivities for the DCB isomers were determined according to the above formula. The obtained results are shown in Table 4.

TABLE 4

| Adsorbent | $\alpha_{p/m}$ | $\alpha_{o/m}$ |
|---|---|---|
| Na—Y | 1.67 | 2.04 |
| K—Y | 1.54 | 2.33 |
| 30% Ag—K—Y | 1.43 | 2.77 |

The adsorption selectivities of the above three adsorbents for the DCB isomers in the presence of a desorbent were determined. As the desorbent, 3,4-dichlorotoluene (hereinafter referred to as "DCT") or chlorobenzene (hereinafter referred to as "CB") was chosen. The feed to be contacted with the adsorbent comprised n-nonane, p-DCB, m-DCB, o-DCB and the desorbent at a weight ratio of 1:1:3:3:7, respectively. Other conditions were the same as described above. The obtained results are shown in Table 5.

TABLE 5

| Adsorbent | Desorbent | $\alpha_{p/m}$ | $\alpha_{o/m}$ |
|---|---|---|---|
| Na—Y | DCT | 1.78 | 1.14 |
| K—Y | CB | 1.15 | 2.22 |
| Ag—K—Y | DCT | 1.50 | 2.80 |
| Ag—K—Y | CB | 1.54 | 4.34 |

As is apparent from the foregoing experimental results, the adsorbents other than the adsorbent of the Ag-K-Y type according to the present invention have in the absence of the desorbent an adsorption selectivity as high as capable of recovering m-DCB from a mixture of DCB isomers, but in these adsorbents, under practical adsorption conditions, that is, in the presence of the desorbent, the value $\alpha_{p/m}$ or $\alpha_{o/m}$ is close to 1 and separation of m-DCB from other DCB isomers is very difficult. In contrast, in case of the adsorbent of the Ag-K-Y type according to the present invention, the adsorptive selectivity is not reduced even in the presence of the desorbent and this adsorbent is very valuable for the industrial separation of m-DCB.

COMPARATIVE EXAMPLE 3

Alumina sol was added as a binder to a powder of a zeolite of the Na-X type ($SiO_2/Al_2O_3$ molar ratio was about 2.5) or the Na-Y type ($SiO_2/Al_2O_3$ molar ratio was 4.8 to 5.2) in an amount of 10% by weight as $Al_2O_3$, a granulation product having a size of 24 to 32 mesh was prepared by extrusion molding from the mixture. The granulation product was dried at 100° C. and calcined at 500° C. for 1 hour to obtain an adsorbent of the Na-X or Na-Y type.

Then, the adsorbent was treated with an aqueous solution of potassium nitrate to replace at least 90% of the sodium cation with the potassium cation and thereby prepare an adsorbent of the K-X or K-Y type.

In order to determine the adsorptive selectivities of the adsorbent for xylenol isomers, about 2 g of the adsorbent calcined at 500° C. for 1 hour and about 2.5 g of a liquid-phase mixture which comprises xylenol isomers were charged in an autoclave having an inner capacity of 5 ml, and was heated at 130° C. for 1 hour while conducting stirring now and then.

The liquid phase mixture charged into the autoclave comprised 2,6-XYOH, 2,4-XYOH, 3,5-XYOH, 3,4-XYOH and n-nonane at a weight ratio of 1:8:1:1:3, respectively.

n-Nonane was added as the internal standard substance for the gas-chromatographical analysis, and n-nonane was substantially inactive relatively to the adsorption under the experimental conditions.

The composition of the liquid phase mixture after the contact with the adsorbent was analyzed by the gas chromatography, and adsorption selectivities α were determined. The obtained results are shown in Table 6.

TABLE 6

| Adsorbent | α 3,5-XYOH/ 2,6-XYOH | α 3,5-XYOH/ 2,4-XYOH | α 3,5-XYOH/ 3,4-XYOH | Order of Adsorbability |
| --- | --- | --- | --- | --- |
| Na—X | 1.26 | 2.32 | 0.76 | 3.4 > 3.5 > 2.6 > 2.4 |
| K—X | 0.82 | 1.11 | 0.47 | 3.4 > 2.6 > 3.5 ≈ 2.4 |
| Na—Y | 2.65 | 1.79 | 0.94 | 3.4 ≈ 3.5 > 2.4 > 2.6 |
| K—Y | 0.82 | 1.10 | 0.44 | 3.4 > 2.6 > 3.5 ≈ 2.4 |

TABLE 6-continued

| Adsorbent | α 3,5-XYOH/ 2,6-XYOH | α 3,5-XYOH/ 2,4-XYOH | α 3,5-XYOH/ 3,4-XYOH | Order of Adsorbability |
| --- | --- | --- | --- | --- |

The adsorbability of 3,5-XYOH to the above-mentioned adsorbents is intermediate among the adsorbabilities of the XYOH isomers. Accordingly, it is impossible to separate and recover 3,5-XYOH as the component capable of being most weakly adsorbed component, that is, the raffinate component.

EXAMPLE 4

The adsorbents prepared in Comparative Example 3 were subjected to the ion exchange treatment 5 times by using an aqueous 0.5N solution of other cation. The solid-liquid ratio was 5 and the temperature was 90° C.

The obtained adsorbents were tested in the same manner as described in Comparative Example 3. The obtained results are shown in Table 7.

TABLE 7

| Adsorbent | α 3,5-XYOH/2,6-XYOH | α 3,5-XYOH/2,4-XYOH | α 3,5-XYOH 3,4-XYOH | Order of Adsorbability |
| --- | --- | --- | --- | --- |
| Oa—Na—X | 1.30 | 1.55 | 0.67 | 3.4 > 3.5 > 2.6 > 2.4 |
| Li—Na—Y | 2.06 | 1.24 | 0.65 | 3.4 > 3.5 > 2.4 > 2.6 |
| Ni—Na—Y | 3.14 | 1.45 | 0.55 | 3.4 > 3.5 > 2.4 > 2.6 |
| Co—Na—Y | 2.79 | 1.60 | 0.52 | 3.4 > 3.5 > 2.4 > 2.6 |
| Co—K—Y | 1.36 | 0.98 | 0.59 | 3.4 > 3.5 ≈ 2.4 > 2.6 |
| Cu—Na—Y | 0.55 | 0.51 | 0.35 | 3.4 > 2.4 ≈ 2.6 > 3.5 |
| Cu—K—Y | 0.70 | 0.69 | 0.50 | 3.4 > 2.4 ≈ 2.6 > 3.5 |

Among the adsorbents shown in Example 4, only the adsorbents containing the copper cation can separate and recover 3,5-XYOH having a high purity as the raffinate component.

EXAMPLE 5

The zeolite of the K-Y type prepared in Comparative Example 3 was subjected to the ion exchange treatment with an aqueous solution of silver nitrate containing a silver ion in an amount corresponding to 20, 30 or 40 mole% of the potassium cation in the zeolite. Some samples were further ion-exchanged with about 5 mole% of a proton (H). The adsorbents were tested in the same manner as described in Comparative Example 3. The obtained results are shown in Table 8.

TABLE 8

| Adsorbent | α 3,5-XYOH/2,6-XYOH | α 3,5-XYOH/2,4-XYOH | α 3,5-XYOH 3,4-XYOH | Order of Adsorbability |
| --- | --- | --- | --- | --- |
| 20% Ag—K—Y | 0.78 | 0.71 | 0.41 | 3.4 >0 2.4 ≈ 2.6 > 3.5 |
| 30% Ag—K—Y | 0.81 | 0.80 | 0.50 | " |
| 30% Ag—(H)—K—Y | 0.57 | 0.57 | 0.37 | " |
| 40% Ag—(H)—K—Y | 0.69 | .76 | 0.46 | " |

The silver cation-containing adsorbents shown in this example can separate and recover 3,5-XYOH having a high purity as the raffinate component.

EXAMPLE 6

The adsorption selectivities of the copper or silver cation-containing adsorbents prepared in Examples 4 and 5 were determined by using a mixture of XYOH isomers containing p- and m-ethylphenols (hereinafter referred to as "EP").

The mixture comprised 2,3-XYOH, 2,4-XYOH, 3,4-XYOH, 3,5-XYOH, P-EP and m-EP at a weight ratio of about 5/5/25/55/5/5, respectively.

The obtained results are shown in Table 9.

TABLE 9

| Adsorbent | α 3,5-XYOH/ 2,3-XYOH | α 3,5-XYOH/ 2,4-XYOH | α 3,5-XYOH/ 3,4-XYOH | α 3,5-XYOH/ p-EP | α 3,5-XYOH/ m-EP |
|---|---|---|---|---|---|
| Cu—Na—Y | 0.55 | 0.44 | 0.45 | 0.51 | 0.76 |
| 30% Ag—(H)—K—Y | 0.24 | 0.28 | 0.30 | 0.16 | 0.30 |

As is apparent from the results shown in Example 6, the copper or silver cation-containing adsorbent according to the present invention can separate and recover 3,5-XYOH as the raffinate component even if ethylphenols are contained in a mixture of XYOH isomers.

EXAMPLE 7

The adsorption selectivities of the 30% Ag-K-Y adsorbent containing a Ag cation prepared in Example 3 were determined by using a mixture of trimethylbenzene (hereinafter referred to as "TMB") isomers. The mixture comprised 1,2,3-TMB, 1,2,4-TMB, 1,3,5-TMB and n-nonane at a weight ratio of 2/2/2/1, respectively. The testing temperature was 130° C. and all other conditions remained substantially the same as mentioned in Example 1.

The obtained results are shown in Table 10.

TABLE 10

| Adsorbent | α 1,2,3-TMB/ 1,3,5-TMB | α 1,2,4-TMB/ 1,3,5-TMB | Order of Adsorbability |
|---|---|---|---|
| 30% Ag—K—Y | 2.95 | 2.78 | 1,2,3-TMB ≧ 1,2,4-TMB > 1,3,5-TMB |

The silver-cation containing adsorbent shown in this example can separate and recover 1,3,5-TMB as the raffinate component.

COMPARATIVE EXAMPLE 4

The adsorption selectivities between TMB isomers of the Na-Y type and K-Y type adsorbents prepared in Example 3 were determined. The testing conditions were substantially the same as employed in Example 7.

The obtained results are shown in Table 11.

TABLE 11

| Adsorbent | α 1,2,3-TMB/ 1,3,5-TMB | α 1,2,4-TMB/ 1,3,5-TMB | Order of Adsorbability |
|---|---|---|---|
| Na—Y | 1.27 | 0.77 | 1,2,3-TMB > 1,3,5-TMB 1,2,4-TMB |
| K—Y | 1.00 | 2.30 | 1,2,4-TMB > 1,3,5-TMB = 1,2,3-TMB |

EXAMPLE 8

The adsorbents of the Ag-K-Y type prepared in the same manner as described in Example 1 were tested for the adsorptive selectivity of the diethylbenzene isomers. The liquid-phase mixture charged comprised n-nonane, p-DEB, m-DEB and o-DEB at a weight ratio of 20/22/54/4. The adsorptive selectivities of the resulting adsorbents for the diethylbenzene isomers were determined in the same manner as described in Example 1. The obtained result are shown in Table 12.

TABLE 12

| Amount of Ag Ion in Treating Liquid [Ag/(K—Y) molar ratio] | $\alpha_{o/m}$ | $\alpha_{p/m}$ |
|---|---|---|
| 0.1 | 2.78 | 1.96 |
| 0.3 | 1.85 | 2.17 |
| 0.4 | 1.85 | 1.54 |
| 0.8 | 1.96 | 1.51 |

COMPARATIVE EXAMPLE 5

The adsorbents of the Na-Y and K-Y prepared in Example 3 were tested in the same manner as described in Example 8. The obtained results are shown in Table 13.

TABLE 13

| Adsorbent | $\alpha_{o/m}$ | p/m |
|---|---|---|
| K—Y | 0.51 | 3.57 |
| Na—Y | 1.22 | 0.84 |

We claim:

1. A process for separating 3,5-xylenol from an isomer mixture containing 3,5-xylenol, which comprises contacting the isomer mixture with an adsorbent of a zeolite of the Y type containing at least one of an Ag cation and a Cu cation, whereby 3,5-xylenol is separated and recovered as a raffinate component, and expelling the isomers adsorbed in the adsorbent by a desorbent to regenerate the adsorbent, said desorbent being selected from the group consisting of alcohols having 3 to 6 carbon atoms and ketones having 4 to 6 carbon atoms.

2. A process according to claim 1, wherein the Y type zeolite adsorbent contains at least one of the Ag cation and the Cu cation in an amount of 5 to 100 mole% of all the cations.

3. A process for separating 3,5-xylenol from an isomer mixture containing 3,5-xylenol, which comprises contacting the isomer mixture with an adsorbent of a zeolite of the Y type containing at least one of an Ag cation and a Cu cation, whereby 3,5-xylenol is separated and recovered as a raffinate component.

* * * * *

UNITED STATES PATENT AND TRADEMARK OFFICE
CERTIFICATE OF CORRECTION

PATENT NO. : 4,769,499
DATED : Sept. 6, 1988
INVENTOR(S) : Kishio Miwa; Yukiko Nagaoka, Takehise Inoue It is certified that error appears in the above-identified patent and that said Letters Patent is hereby corrected as shown below:

Column 9, line 58 (or Table 11, line 6) add > (greater than symbol) before numbers.

Signed and Sealed this

Twentieth Day of February, 1990

*Attest:*

JEFFREY M. SAMUELS

*Attesting Officer*     *Acting Commissioner of Patents and Trademarks*